US006743188B1

(12) United States Patent
Littmann et al.

(10) Patent No.: US 6,743,188 B1
(45) Date of Patent: Jun. 1, 2004

(54) CUSHION WITH SOFT ELASTIC MATERIAL

(75) Inventors: Alexander Littmann, Isernhagen (DE); Reinhold Schneider-Nieskens, Adendorf (DE); Hans Georg Blau, Burgwedel (DE)

(73) Assignee: Thämert Orthopädische Hilfsmittel GmbH & Co., KG, Burgwedel (DE)

( * ) Notice: Subject to any disclaimer, the term of this patent is extended or adjusted under 35 U.S.C. 154(b) by 549 days.

(21) Appl. No.: 09/675,163

(22) Filed: Sep. 29, 2000

(30) Foreign Application Priority Data

Oct. 5, 1999 (DE) ........................ 299 17 514 U

(51) Int. Cl.⁷ .................. A61F 5/00; A61F 13/00
(52) U.S. Cl. .................. 602/1; 602/20; 602/62
(58) Field of Search .................. 128/845, 846, 128/869, 878, 879, 888, 893, 894; 602/1, 41, 42, 6, 8, 60, 61, 62

(56) References Cited

U.S. PATENT DOCUMENTS

| 4,287,885 A | 9/1981 | Applegate |
| 5,027,801 A | 7/1991 | Grim |

FOREIGN PATENT DOCUMENTS

| EP | 0 934 732 | 8/1999 |
| WO | WO 97/24085 | 7/1997 |
| WO | WO 99/09917 | 3/1999 |

*Primary Examiner*—Kim M. Lewis
(74) *Attorney, Agent, or Firm*—Collard & Roe, P.C.

(57) ABSTRACT

A cushion having at least one soft elastic region for use with orthopedic devices. The soft elastic region is detachably arranged on the cushion so that the cushion or the soft elastic region can be replaced when it is worn out while still using the other part.

13 Claims, 3 Drawing Sheets

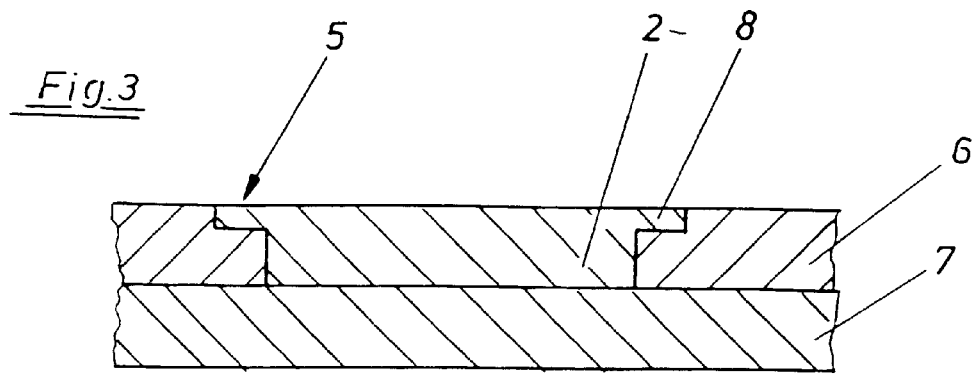
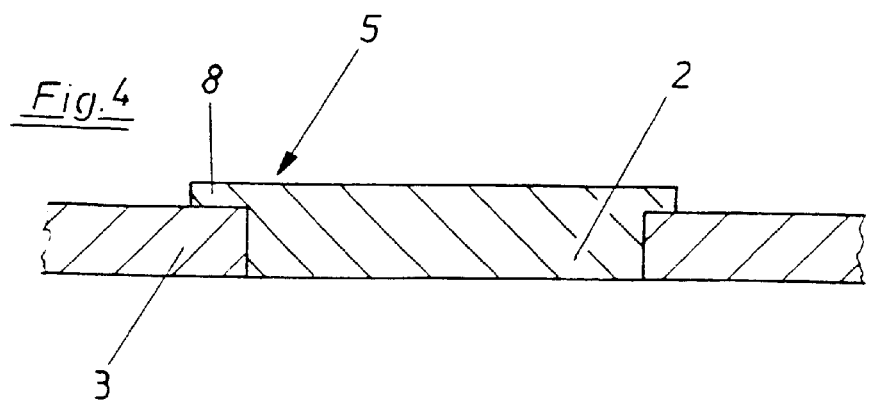
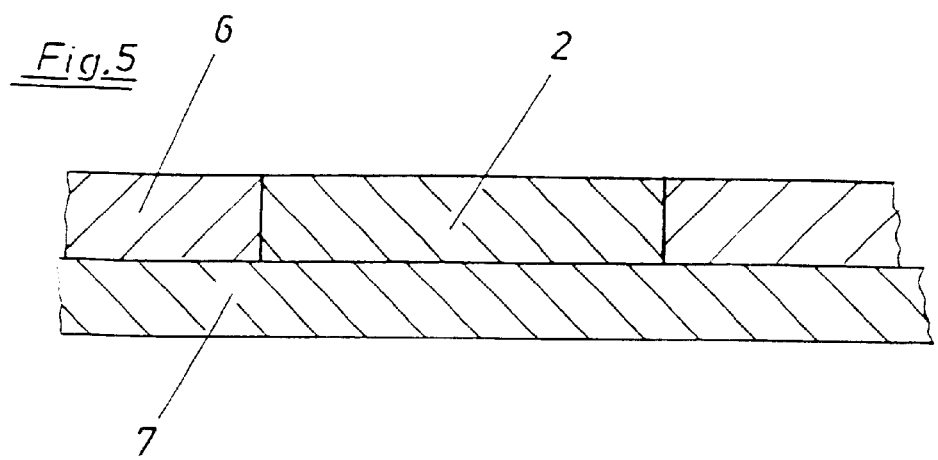

CUSHION WITH SOFT ELASTIC MATERIAL

BACKGROUND OF THE INVENTION

1. Field of the Invention

The invention relates to a cushion, and method for producing the same, with at least one soft elastic region. More specifically, the invention relates to a felt cushion with a silicone pad, for use with orthopedic devices.

2. The Prior Art

It is known that such cushions may be used in orthopedic devices, e.g., in epicondylitis braces. Therefore, a felt cushion is adapted to the shape of the epicondylitis brace. Silicone spots are applied to the skin of the user of the orthopedic devices to prevent the cushion from slipping. Recesses are usually cut into the felt cushion and soft elastic regions or silicone castings are glued into these recesses.

Such orthopedic devices are known for example from WO 97/24085 and WO 99/09917.

SUMMARY OF THE INVENTION

An object of the present invention is to create a cushion which can be used for an especially long period of time. In addition, the object of this invention is also to provide a method of producing such a cushion.

According to the invention, the soft elastic region is detachably attached to the cushion. This permits a reduction of material because the component of the cushion, namely either the cushion itself or the soft elastic region which is subject to less wear, can be reused. Therefore, if the soft elastic region, in particular a silicone pad, has become worn due to frequent use it can be removed from the cushion and replaced by a new one. Furthermore, the cushion area can be replaced if it is subject to greater wear. Numerous fastening options are available for arranging the cushion on the soft elastic region. The soft elastic region preferably has a retaining element with which the soft elastic region is attached to the cushion. It is also possible for the soft elastic region to be designed such that it is inserted into a recess in the cushion and remains there merely by friction. In this case, the soft elastic region would have to be designed to be exactly the same size or slightly larger than the corresponding recess.

However, it is preferable to design the soft elastic region in the form of a silicone casting, so that the retaining element projects beyond the dimensions of the other soft elastic region. The retaining element is designed as a retaining flange which is provided in at least two locations on the soft elastic region and is disposed on the upper edge of the soft elastic region. This allows the soft elastic region to be inserted into a corresponding recess in the cushion and the retaining flanges provided on the upper edge are in contact with the cushion. Therefore, the soft elastic region is designed thicker than the cushion by the thickness of the retaining flange. In a preferred embodiment, the retaining flange is designed peripherally and with a through-passage, so that a retaining effect is achieved in the entire soft elastic region. The retaining flange is arranged on the side facing away from the user's body, so that a flush seal is on the side facing away from the user's body.

In another preferred embodiment, a VELCRO®-type hook and loop element is provided as the retaining element. If VELCRO® hook and loop tape is provided on the soft elastic region, then a fleece is preferably arranged on the cushion. The VELCRO®-type hook and loop clement is preferably designed to project above the soft elastic region so that the VELCRO®-type hook and loop element can be engaged with a corresponding strip on the back side of the cushion. The soft elastic region can be inserted into a recess in the cushion and detachably attached to the cushion with the VELCRO®-type hook and loop element. The soft elastic region can then be detached as needed and replaced by a new soft elastic region. As an alternative, it is also possible to provide the VELCRO®-type hook and loop element on the back of the soft elastic region. The VELCRO®-type hook and loop closure is then established with the orthopedic device used with the cushion.

The VELCRO®-type hook and loop element can be attached to the soft elastic region in various ways. The VELCRO®-type hook and loop element is preferably bonded to the soft elastic region. This means that the VELCRO®-type hook and loop element forms with the soft elastic region a bordering layer or a boundary layer approximately 1 mm thick in which the soft elastic region is drawn into the VELCRO®-type hook and loop element.

To produce such a cushion, the, soft elastic region is designed from a cast. To form the casting, a free flowing material is poured into a mold, the VELCRO®-type hook and loop element is brought in contact with the material while it is still free-flowing, and the free-flowing material is then vulcanizec and bonder to the VELCRO®-type element. Therefore, the VELCRO®-type hook and loop clement is brought in contact with the material while still liquid before it undergoes vulcanization. The viscosity of the material and the vulcanization time must be selected so that the free-flowing material fuses with the VELCRO®-type hook and loop element, but does hot completely permeate it. As an alternative, the VELCRO®-type hook and loop element can be glued to the soft elastic region. Suitable adhesives include mixed adhesives, reactive adhesives, solvent adhesives or hot-melt adhesive, e.g., hot-melt adhesive films.

The VELCRO®-type element can be attached to the soft elastic region in various ways. The VELCRO®-type element is preferably bonded to the soft elastic region. This means that the VELCRO®-type element forms with the soft elastic region a bordering layer or a boundary layer approximately 1 mm thick in which the soft elastic region is drawn into the VELCRO®-type element.

To produce such a cushion, the soft elastic region is designed from a cast. To form the casting, a free-flowing material is poured into a mold, the VELCRO®-type element is brought in contact with the material while it is still free-flowing, and the free-flowing material is then vulcanized and bonded to the VELCRO®-type element. Therefore, the VELCRO®-type element is brought in contact with the material while still liquid before it undergoes vulcanization. The viscosity of the material and the vulcanization time must be selected so that the free-flowing material fuses with the VELCRO®-type element, but does not completely permeate it. As an alternative, the VELCRO®-type element can be glued to the soft elastic region. Suitable adhesives include mixed adhesives, reactive adhesives, solvent adhesives or hot-melt adhesives, e.g., hot-melt adhesive films.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 3 shows a cross-sectional view of the soft elastic region during the production process;

FIG. 4 shows a cross section through a cushion with a soft elastic region produced according to FIG. 3;

FIG. 5 shows a cross section through,an alternative embodiment of a soft elastic region according to the invention during the production process;

DETAILED DESCRIPTION OF PREFERRED EMBODIMENTS

Figure 1:
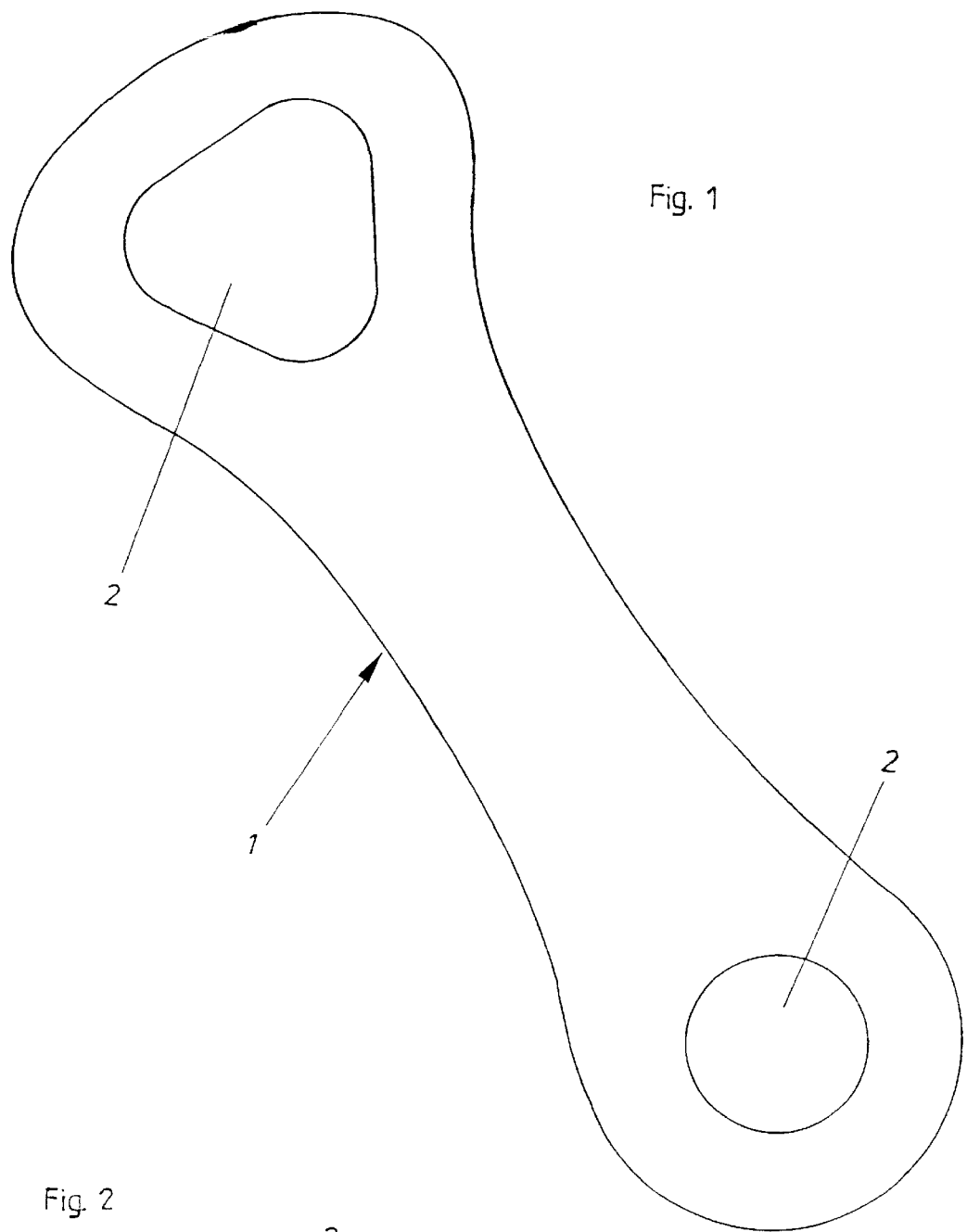
FIG. 1 shows a top view of a cushion with a soft elastic region.

Referring now in detail to the drawings and, in particular, in FIG. 1 there is shown a cushion 1 intended for use in a epicondylitis brace. The shape of the cushion is adapted to the shape of the epicondylitis brace, and soft elastic regions 2 are arranged on the enlarged end areas so that they come in contact with the skin and prevent cushion 1 from slipping.

Figure 2:
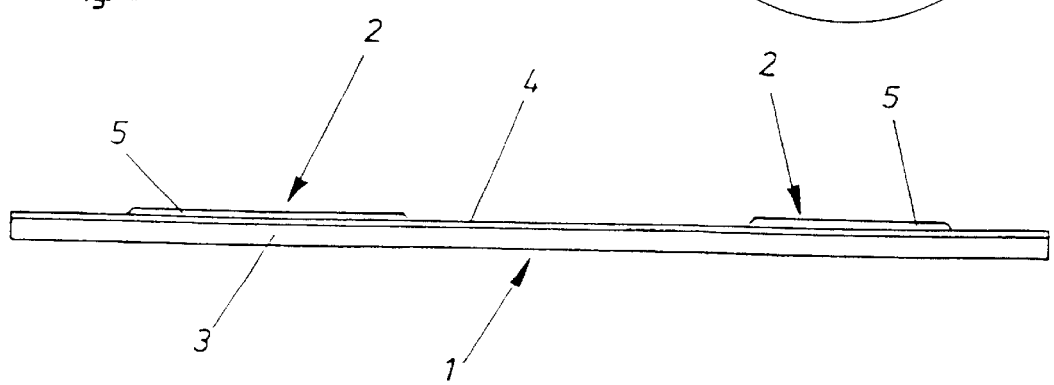
FIG. 2 shows a side view of a cushion with a soft elastic region according to FIG. 1.

FIG. 2 shows a side view of cushion 1. In its lower area, cushion 1 contains a felt cushion 3 on which fleece 4 is arranged. Fleece 4 is designed to engage with a hook strip to form a VELCRO®-type closure. Soft elastic regions 2 may be designed so that they have a retaining element 5 which projects above cushion 1. Retaining element 5 is arranged on the side of cushion 1 facing away from the user's body.

FIG. 3 shows a cross sectional view through soft elastic region 2 during the production process. A mold 6 rests on a heating plate 7. A liquid material, in particular liquid silicone, is introduced into this mold 6 and then vulcanizes in the mold to assume the shape indicated. The vulcanization time depends on the temperature, which is controlled by heating plate 7, the catalyst content, and the original consistency or viscosity of the material cast in the mold. The soft elastic region is produced as one piece with peripheral retaining flange 8 formed in a corresponding recess in mold. Retaining flange 8 runs along the upper edge area of soft elastic region 2.

FIG. 4 shows a cross section through soft elastic region 2 detachably arranged in felt cushion 3. Thus, soft elastic region 2 can be inserted and removed through retaining flange 8 on felt cushion 3. Secure handling is ensured when the side of felt cushion 3 on which retaining flange 8 is located is facing the user. This prevents unintentional detachment of soft elastic region 2. If a continuous closure of felt cushion 3 and soft elastic region 2 is desired, the bottom side should face the user. This almost completely rules out unintentional slippage of soft elastic region 2 from felt cushion 3 because the cushion is usually used together with an orthopedic device, such as an epicondylitis brace with the back of soft elastic region 2 in contact with in. The back of soft elastic region 2 may be attached to the epicondylitis brace, e.g., by a VELCRO®-type hook and loop closure.

Figure 6:
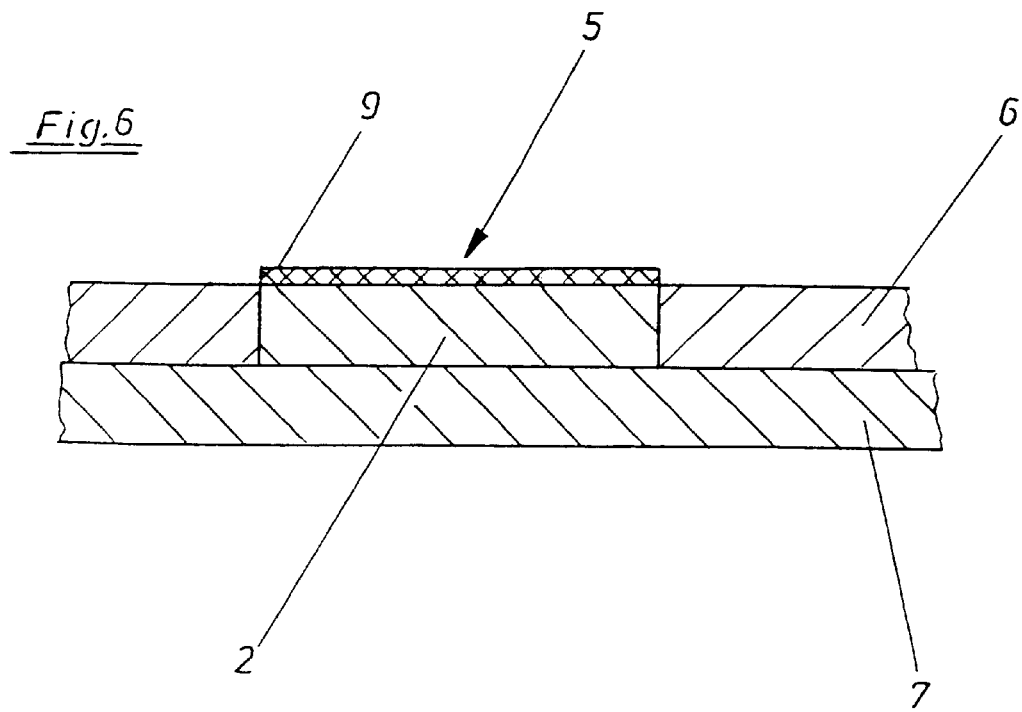
FIG. 6 shows a diagram according to FIG. 5 in an advanced stage of the process.

FIGS. 5 and 6 show cross sections through a cushion with a soft elastic region during two different steps of the method for production of the cushion. FIG. 5 shows a mold 6 which is resting on a heating plate 7 and in which a soft elastic region 2 is produced by filling it with liquid silicone. A plurality of molds 6 are preferably arranged on heating plate 7 so that a plurality of soft elastic regions 2 can be produced at the same time. This is also true of the embodiment of the method according to FIG. 3.

FIG. 6 shows a retaining element 5, formed by a VELCRO®-type element 9, applied to the casting according to FIG. 5 while still molten. VELCRO®-type hook and loop element 9 is either a fleece or a VELCRO® hook and loop tape, so that it can be brought into VELCRO®-type hook and loop closure with a corresponding VELCRO® hook and loop strip or fleece. VELCRO®-type hook and loop element 9 is applied to the casting while still hot so that the liquid material is absorbed into the VELCRO®-type hook and loop element 9 about 1 mm, and is fused thereto. Soft elastic region 2 is then vulcanized by heating plate 7, and then soft elastic region 2 can be removed from mold 6 and used in a cushion. VELCRO®-type hook and loop element 9 is attached to the orthopedic device according to the embodiment shown. Soft elastic region 2 can also be used with cushions which do not have any recesses but instead have a section corresponding to VELCRO®-type hook and loop element 9. The soft elastic region is then applied directly to the cushion by a VELCRO®-type connection and projects slightly above it. As an alternative, it is also possible to use a VELCRO®-type hook and loop element 9 which projects beyond the edges of soft elastic region 2 in its outside dimensions.

Figure 7:
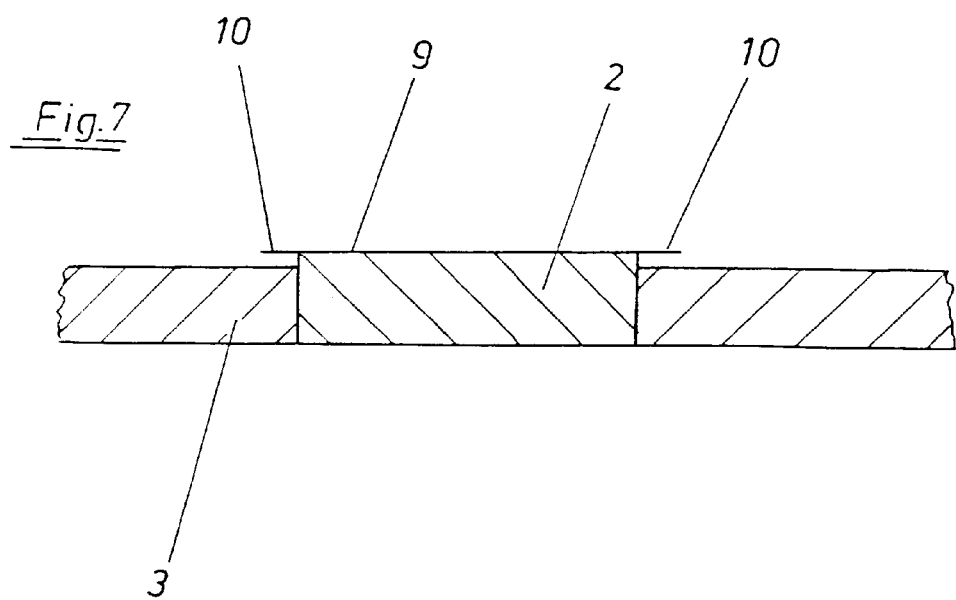
FIG. 7 shows a cross section through a cushion with another embodiment of the soft elastic region.

A cross section through soft elastic region 2 is felt cushion 3 is shown in FIG. 7, VELCRO®-type hook and loop element 9 projects above soft elastic region 2 with a projection 10. By using a VELCRO®-type hook and loop closure, this projection 10 can be attached with its VELCRO®-type hook and loop element facing downward to the felt cushion 3 or a corresponding fleece or VELCRO® strip hook and loop which is arranged on felt element 3. Therefore, soft elastic region 2 can be detachable from the cushion.

Accordingly, while only a few embodiments of the present invention have been shown and described, it is to be understood that many changes and modifications may be made there unto without departing from the spirit and scope of the invention.

What is claimed is:

1. A cushion for use with an epicondylitis brace, said cushion being adapted to the shape of an epicondylitis brace such that said cushion contains enlarged end areas, and comprising at least one soft elastic region, detachably arranged on at least one end area of the cushion.

2. The cushion according to claim 1, wherein said soft elastic region comprises at least one rotaining element.

3. The cushion according to claim 2, wherein said retaining element projects beyond the dimension of the soft elastic region.

4. The cushion according to claim 2, wherein said retaining element comprises a hook and loop-type element.

5. The cushion according to claim 4, wherein said hook and loop-type element projects above said soft elastic region.

6. The cushion according to claim 4, wherein said hook and loop-type element is disposed on a backside of said soft elastic region.

7. The cushion according to claim 4, wherein said hook and loop-type element is fused to said soft elastic region.

8. The cushion according to claim 4, wherein said hook and loop-type element is glued to said soft elastic region.

9. The cushion according to claim 1, wherein said soft elastic region is formed from silicone casting.

10. The cushion according to claim 1, wherein said soft elastic region comprises a retaining flange.

11. The cushion according to claim 10, wherein said retaining flange is disposed peripherally and comprises a through passage.

12. The cushion according to claim 10, wherein soft elastic region and said retaining flange is formed as one piece.

13. A method of producing a cushion used with orthopedic device having a detachable soft elastic region comprising the steps of:

pouring a free-flowing material into a mold producing a cast;

placing a hook and loop-type element into said free-flowing material; and vulcanizing and fusing said free-flowing material to said hook and loop-type element.

* * * * *